United States Patent

Pelz

[19]

[11] Patent Number: 5,964,720
[45] Date of Patent: Oct. 12, 1999

[54] METHOD AND SYSTEM FOR MONITORING THE PHYSIOLOGICAL CONDITION OF A PATIENT

[75] Inventor: Shmuel Pelz, Katzrin, Israel

[73] Assignee: Adaptivity Devices Ltd., Katzrin, Israel

[21] Appl. No.: 08/979,938

[22] Filed: Nov. 26, 1997

[30] Foreign Application Priority Data

Nov. 29, 1996 [IL] Israel ........................................ 119721

[51] Int. Cl.$^6$ .................................................. A61B 5/103
[52] U.S. Cl. .......................... 600/595; 600/483; 600/500; 600/537
[58] Field of Search .................................. 600/500, 501, 600/527, 534, 595, 481, 483, 484

[56] References Cited

U.S. PATENT DOCUMENTS

| | | | |
|---|---|---|---|
| 4,299,233 | 11/1981 | Lemelson | 600/500 |
| 4,320,766 | 3/1982 | Alihanka et al. | 600/595 |
| 4,381,788 | 5/1983 | Douglas | 600/534 |
| 4,595,023 | 6/1986 | Bonnet | 600/595 |
| 4,657,025 | 4/1987 | Orlando | 600/527 |
| 4,657,026 | 4/1987 | Tagg | 600/534 |
| 4,738,264 | 4/1988 | Orlando | 600/527 |
| 4,836,215 | 6/1989 | Lee | 600/527 |
| 4,884,578 | 12/1989 | Morgenstern | 600/527 |
| 4,889,131 | 12/1989 | Salem et al. | 600/534 |
| 4,971,065 | 11/1990 | Pearce | 600/595 |
| 5,131,399 | 7/1992 | Sciarra | 600/534 |
| 5,447,167 | 9/1995 | Fleischaker | 600/595 |
| 5,448,996 | 9/1995 | Bellin et al. | 600/595 |
| 5,479,932 | 1/1996 | Higgins et al. | 600/534 |
| 5,684,460 | 11/1997 | Scanlon | 600/534 |
| 5,749,365 | 5/1998 | Magill | 600/527 |

FOREIGN PATENT DOCUMENTS 2 261 290   5/1993   United Kingdom ......... A61B 5/0205

OTHER PUBLICATIONS

Polo, O. et al. "The Validity of the Static Charge Sensitive Bed in Detecting Obstructive Sleep Apnoeas." *European Respiratory Journal*, v1, pp. 300–336, 1988.

*Primary Examiner*—Cary O'Connor
*Assistant Examiner*—Charles Marmor, II
*Attorney, Agent, or Firm*—Oliff & Berridge, PLC

[57] ABSTRACT

A system for the monitoring of a patient's physiological condition, including a measuring device for measuring the mechanical activity of a patient's body, including a module for detecting mechanical vibrations and transmitting same to a sensing element for converting the mechanical movements into electric signals. A device for transmitting the electric signals for processing the electric signals and separating from them cardiac, respiration and body movement signals. A device for measuring the pulse wave propagation rate. A device for determining the characteristics and derived parameters of cardiac and respiratory cycles, as well as for storing and displaying the data. A comparator for comparing parameters of the data with predetermined parameters and a device for actuating an alarm signal when signals of the data exceed a preset range.

20 Claims, 7 Drawing Sheets

METHOD AND SYSTEM FOR MONITORING THE PHYSIOLOGICAL CONDITION OF A PATIENT

FIELD OF THE INVENTION

The present invention relates to a method and system for monitoring the physiological condition of a patient's body. The invention is particularly useful in applications at home, at workplaces, and in medical institutions.

BACKGROUND OF THE INVENTION

Methods and systems are known for monitoring the cardiac and respiratory activity of a patient and for generating an alarm in the event of cessation of breathing known as apnea, heartbeat cessation, or when the observed cardiovascular activity surpasses a preset limit.

Such methods and systems find application in medical institutions for monitoring the condition of patients having respiratory or cardio-vascular diseases; monitoring newborn babies who may be susceptible to SIDS (Sudden Infant Death) syndrome, and in other clinical cases. As a rule, such monitoring is carried out by means of passive collection of information regarding a patient's condition, without attaching electrodes directly to the patient's body.

A method and system is known for round-the-clock monitoring of patients afflicted with OSAS (Obstructive Sleep Apnea) syndrome, which system comprises a special mattress with embedded sensors, electronic filters, a polygraph, etc. [see O. Polo, et al., "The Validity of the Static Charge Sensitive Bed in Detecting Obstructive Sleep Apneas," *European Respiration Journal,* Vol. 1, pp. 330–336 (1988)]. This method and system permit the recording of various movements of a sleeping patient, respiratory and cardiovascular deviations, and the like.

In U.S. Pat. No. 4,884,578, entitled "Apparatus for Monitoring Respiration and Cardiac Activity," there is disclosed an apparatus including a special bed mounted on a support suspended by cords or a universal joint and a device for restoring the bed to a normal position. Vertically and horizontally oriented sensors are embedded in the bed and connected to recording devices, permitting monitoring of a wide range of respiratory and cardiac activities.

In U.S. Pat. No. 4,381,788, entitled "Method and Apparatus for Detecting Apnea," there is described a monitor comprising a capacitance-type transducer pad, including two capacitor plates with resilient dielectric material between them and a special sensitive layer adapted to respond to the patient's respiratory motion. The pad is connected via an electric circuit to recording devices. A change of distance between the capacitor plates in response to the patient's movements causes a change of parameters in the sensor's electric circuit. The transduced signal is amplified, delayed for a certain, preset period of time and then, if preset parameters are exceeded, generates an alarm.

All of the above-mentioned methods and devices are complicated, expensive, require complicated instruments and can be applied only to patients confined to their beds and monitored under clinical conditions.

U.S. Pat. Nos. 4,657,025 and 4,738,264, entitled "A Heart and Breathing Alarm Monitor" disclose a monitor comprising a contactless sensor placed on a conventional bed away from a patient and having enhanced sensitivity in the vertical direction, a measuring transducer with electronic filters, and a recording device. The sensor detects the vertical vibrations of the bed produced by the patient's heartbeat and breathing functions, converts the detected vibrations into an electric signal and transmits the latter to the recording device. The device compares the obtained signal with preset circuits and, in the event the signals exceed a preset value, sets off an alarm. This monitor, however, can only be used on a patient confined to a bed and does not provide sufficient noise filtration. Moreover, its functional possibilities are rather limited. In particular, it cannot measure the rate of pulse wave propagation, which reflects the dynamics of the average arterial pressure.

It is an object of the present invention to provide general-purpose methods and devices for monitoring the physiological condition, not only of ill, but also of healthy, persons in clinical, ambulatory, home and working environments, which methods do not limit a person's activity in performing a job of average intensity in a sitting position. On the basis of such monitoring, the dynamics of the person's physiological condition and the necessity for its regulation or medical examination could be recognized.

It is a further object of the present invention to provide a method for measuring the rate of pulse wave propagation, correlated with the dynamics of a patient's average arterial pressure.

A still further object of the present invention is to provide a small, highly sensitive device for monitoring a patient's physiological condition which provides a more satisfactory filtration of noise, and which is of moderate cost.

SUMMARY OF THE INVENTION

In accordance with the present invention, there is provided a method of monitoring the physiological condition of a patient's body, comprising the steps of obtaining signals representing the mechanical activity and movement of the body from two or more detecting and sensing means not secured to the body and spaced apart from each other; removing signals associated with the movements of the body from the obtained signals; separating signals possibly associated with cardiac and/or respiratory activity from the obtained signals; determining propagation rates of the pulse waves of cardiac and respiration activities by determining the shift of the obtained cardiac and respiration signals; comparing the signals representing propagation rates with propagation rate signals obtained from an earlier measurement of the same body; removing those signals which are not characteristic of the wave propagation rates of said body; determining the cardiac and respiratory rhythm parameters from the remaining signals; comparing said parameters with parameters obtained from an earlier measurement of the same body, as well as with predetermined parameters; separating and removing parameters which differ from said predetermined parameters; storing, displaying and comparing the separated parameters with parameters obtained from said earlier measurements, and generating an alarm when one of the parameters exceeds a preset range.

The invention further provides a system for the monitoring of a patient's physiological condition, comprising means for measuring the mechanical activity of a patient's body, including at least one means for detecting mechanical vibrations and transmitting the same to one or more sensing elements for converting the mechanical movements into electric signals; means for transmitting said electric signals; means for processing said electric signals and separating therefrom cardiac, respiration and body movement signals; means for measuring the pulse wave propagation rate; means for determining the characteristics and derived parameters of cardiac and respiratory cycles, as well as for storing and displaying data relating thereto; means for comparing parameters of the obtained data with predetermined parameters, and means for actuating an alarm signal when signals of said obtained data exceed a preset range.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

In the drawings:

FIG. 1 is a basic block diagram of the monitoring system according to the present invention;

DESCRIPTION OF PREFERRED EMBODIMENTS

Referring now to FIG. 1, there is illustrated a system for monitoring the physiological condition of a patient. The system comprises one or several detectors 1 for detecting the mechanical vibrations prevailing near a patient lying in a bed or sitting in an armchair. Each detector 21 for detecting mechanical vibrations comprises a rigid or flexible conductor 1 such as a plate, a strip or a membrane, in combination with a sensor 2. The conductors 1 are connected to sensors 2 and further electrically connected to a processor 3 and a transmitter 4.

Further shown are a receiver 6 for receiving the signals transmitted by a transmitter 4, either via wires, or wirelessly via radio or infrared transmission. The receiver 6 is connected to means for processing the received signals. Such means may include a circuit 7 for processing electric signals and separating therefrom cardiac, respiratory and movement signals, a circuit 8 for measuring the rate of pulse wave propagation, a circuit 9 for removing false cardiac and respiratory signals, and a circuit 10 for determining the characteristics and derived parameters of cardiac and respiration cycles, as well as of the patient's movements. There are also provided a circuit 11 for information storage and display and a circuit 12 for comparing and generating an alarm, e.g., an audible alarm sounding via loudspeaker 14. The means for processing electric signals are known per se and may be constituted by a personal computer 13.

Figure 2:
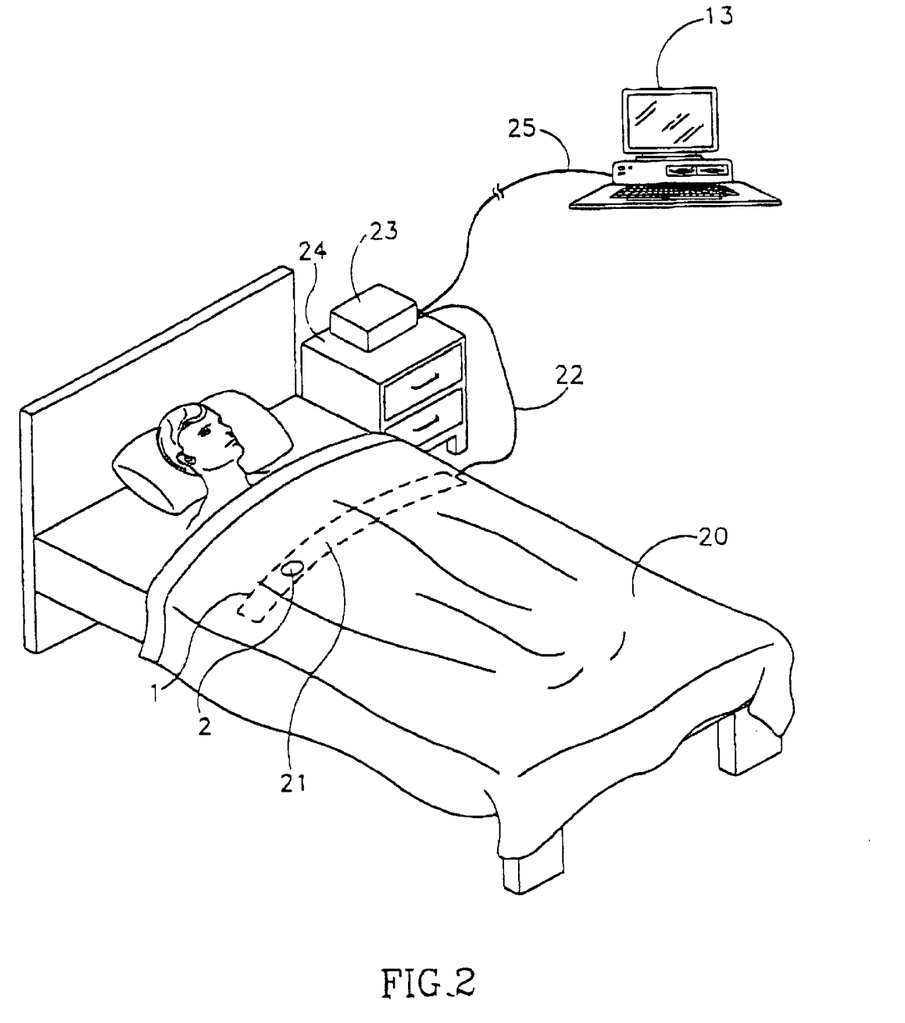
FIG. 2 illustrates the system of the present invention arranged in conjunction with a patient's bed.

FIG. 2 is a diagram illustrating the system of the present invention arranged at a patient's bed. Shown are the detector 21 and comprising a sensor 2 and a single strip-like conductor 1 disposed on bed 20. Detector 21 communicates via cable 22 with a microprocessor 23 placed on table 24 near bed 20. A cable 25 connects the microprocessor 23 to the computer 13. Functions 7–12 (FIG. 1) may be performed by microprocessor or computer (or partly by microprocessor and partly by computer). The processor 3 and microprocessor 23 may be designed as a single unit.

Figure 3:
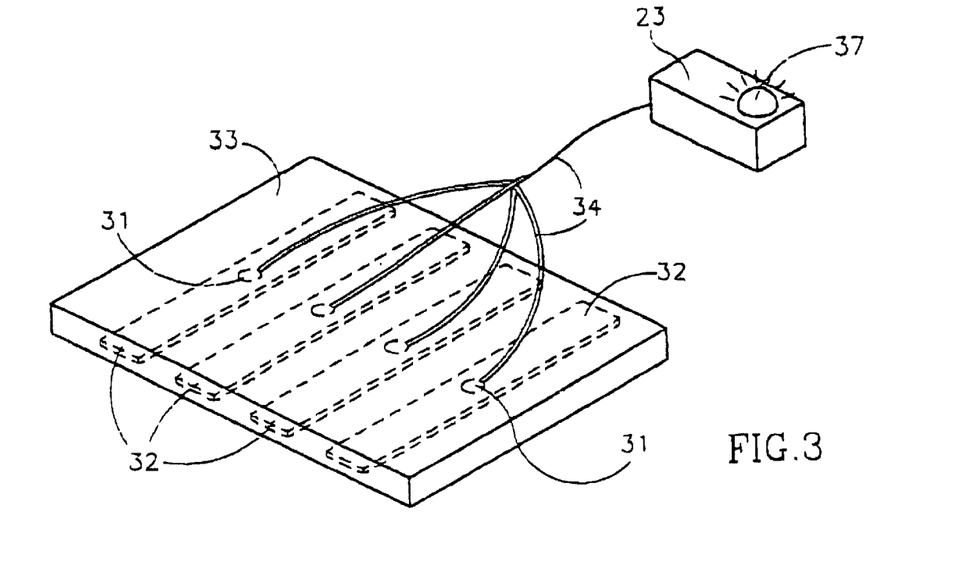
FIG. 3 is a schematic view of the system used in conjunction with a mattress.
Figure 4:
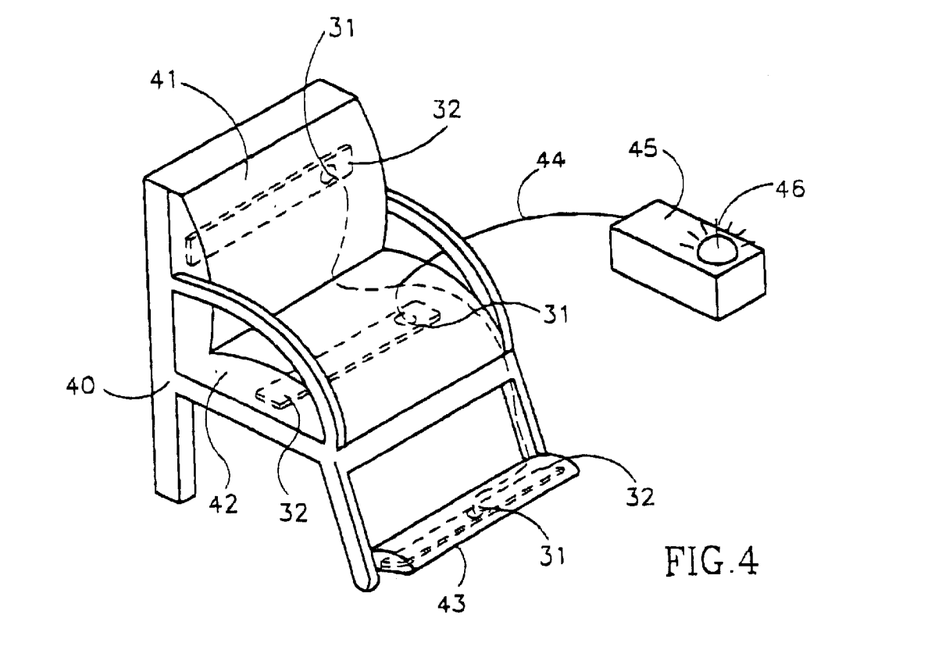
FIG. 4 is a schematic view of the system utilized in conjunction with an armchair.

FIGS. 3 and 4 show other possible modifications in disposing the conductors and sensors for detecting mechanical vibrations. Accordingly, in FIG. 3, there are illustrated several detectors comprising conductors 32 to which sensors 31 are glued. Conductors 32 are embedded in the mattress 33 of a bed (not shown). Cables 34 connect sensors 31 with the microprocessor 23. Means 37 serve as a visual alarm, which is especially suitable for use with a crib for monitoring an infant's physiological activities, irrespective of his or her position within the crib.

In the armchair 40, shown in FIG. 4, the detectors 32 for detecting mechanical vibrations are embedded in the backrest 41, the seat 42 and in the footrest 43. The units are connected via cable 44 with a microprocessor 45, which is provided with a radio device 46 for transmitting signals to a computer (not shown).

Figure 5:
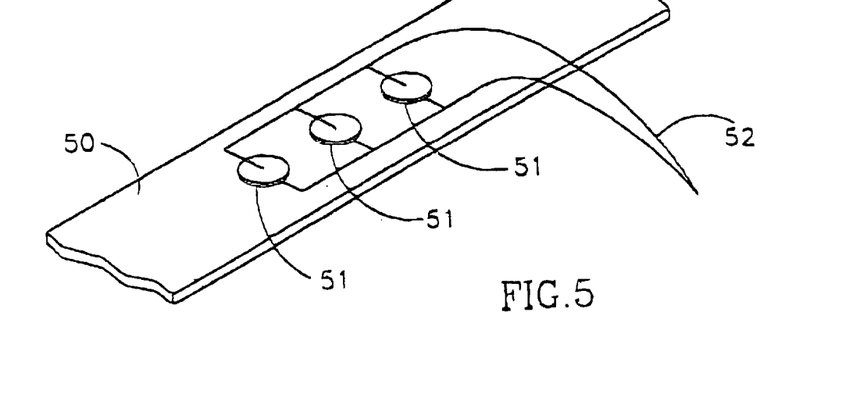
FIGS. 5–10 are schematic representations of different embodiments of means for detecting mechanical vibrations.

In FIGS. 5 to 10, there are shown various embodiments of detectors comprising conductors and sensors for detecting mechanical vibrations. Seen in FIG. 5 is a conductor 50 for detecting mechanical vibrations, upon which sensing elements 51 e.g., crystals, are mounted. A cable 52 connects sensing elements 51 with a micro-processor (not shown). According to the embodiment of FIG. 5, the detectors 50 for detecting mechanical vibrations are relatively thin and provide improved reliability.

Figure 6:
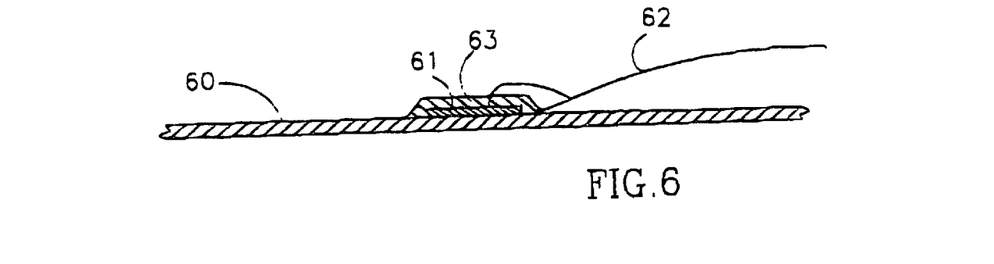

A different embodiment is illustrated in FIG. 6. The sensor 61 is constituted of a piezoelectric crystal and is glued or otherwise affixed to conductor 60 and connected via a cable 62 to a microprocessor (not shown). The sensor 61 is protected against moisture by an adhesive film 63.

Figure 7:
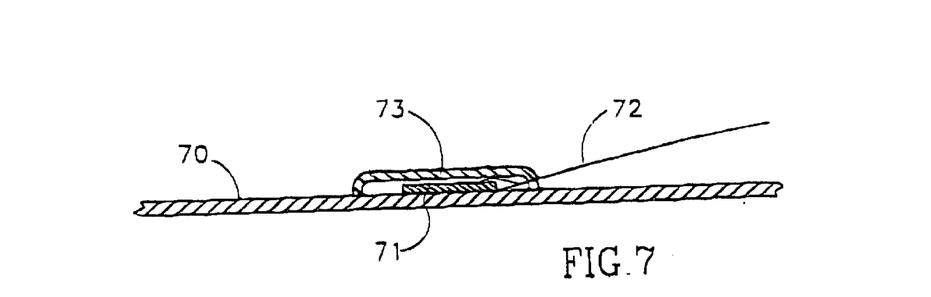

FIG. 7 illustrates a piezoceramic sensor 71 mounted on a conductor 70. The sensor 71 is protected by a casing 73, and provided with a cable 72 for connection to a microprocessor (not shown). The detectors and sensors may be combined to form a flat piezoelectric element or film.

Figure 8:
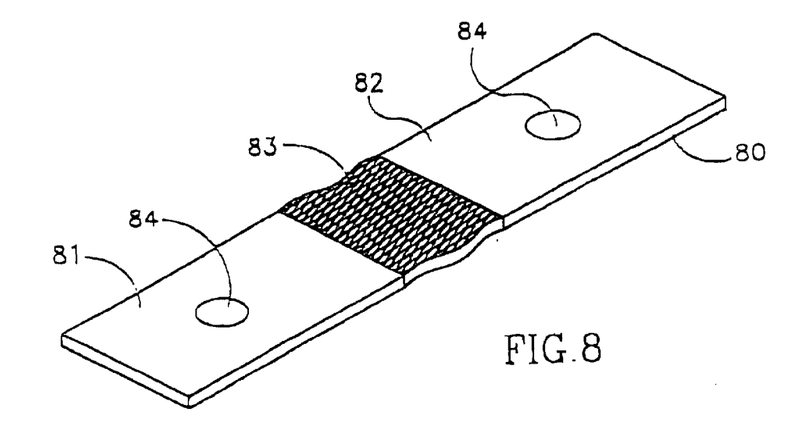

In FIG. 8 there is shown a detector 80, configured as a ruler consisting of two conductors 81 and 82, connected to one another via a flexible element 83.

Figure 9:
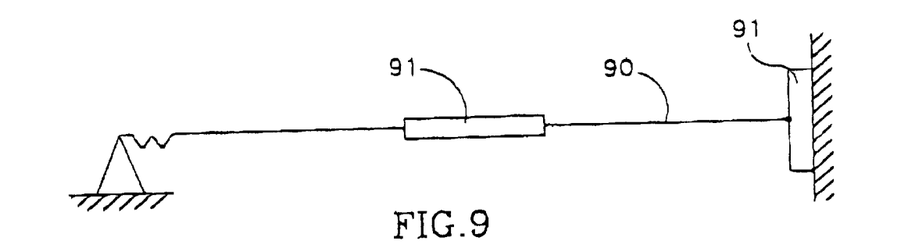
Figure 10:
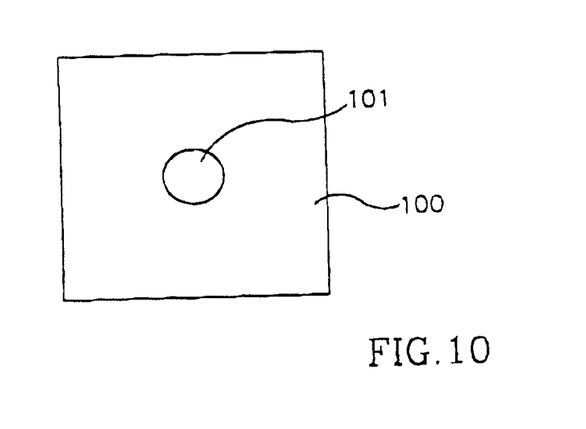

Still further embodiments of conductor and sensor arrangements are shown in FIGS. 9 and 10. The arrangement of FIG. 9 includes a string 90 which acts as a conductor and a sensor 91 threaded thereon or secured thereto. A plate-shaped conductor 100 with an embedded sensor 101 is shown in FIG. 10.

All types of detectors, including all those described herein, may also be made as and constitute a furniture member, e.g., a mattress, a bed, a back or a leg of a bed, a seat back or an armchair footrest, or they may be placed in a bed or made as a flexible member such as a ruler or a film strip embedded in an article of bedding, such as a blanket, a pillow or even a sheet. It is also possible to arrange measuring devices in the shape of floor elements disposed at an armchair (not shown). The measuring devices may also be put into a pen (not shown), or into any other device which a person holds in his hand during the course of work.

Figure 11:
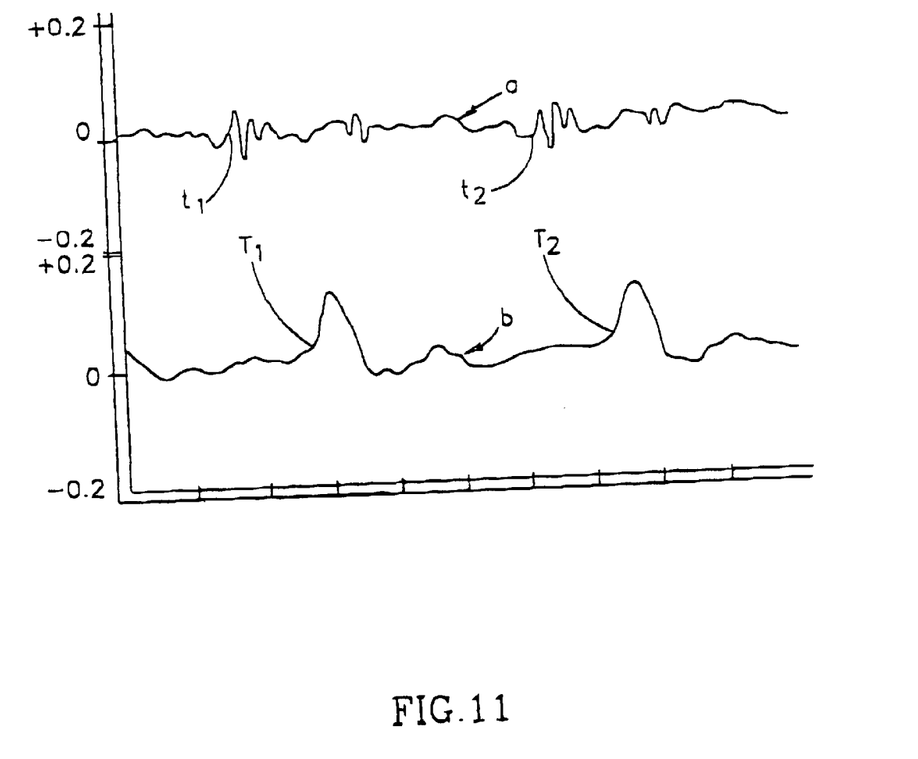
FIGS. 11 and 12 are schematic diagrams showing traces of electric waves produced during the processing of monitored signals.
Figure 12:
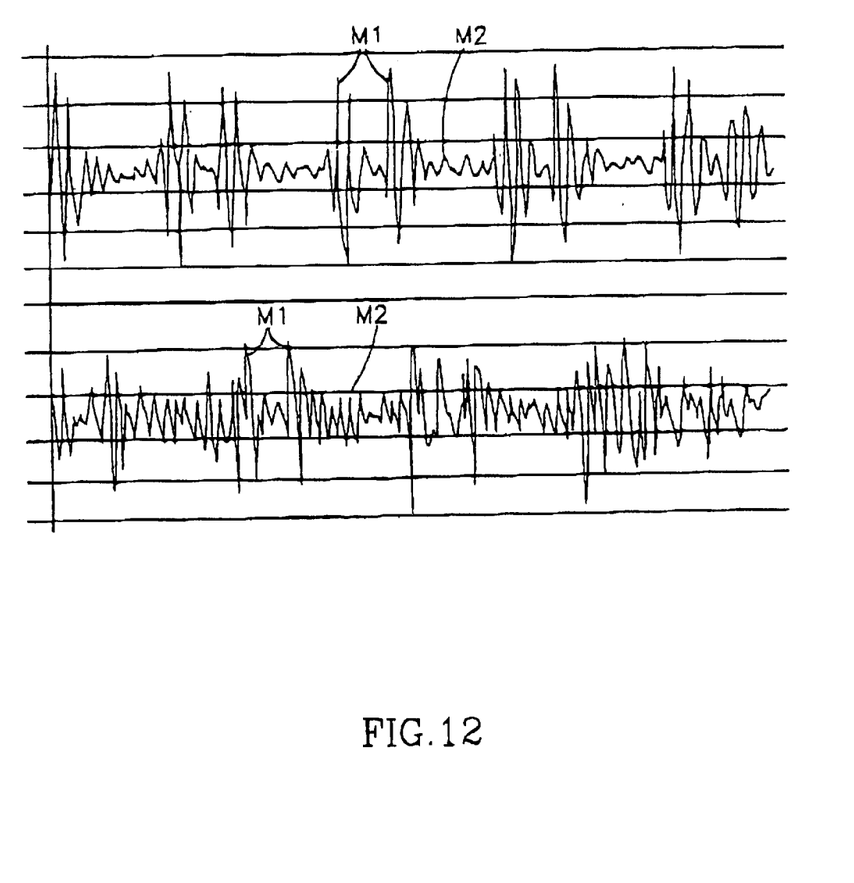

Schematic diagrams of signals, representing the electric waves of a monitored patient at different stages of processing, are shown in FIGS. 11 and 12.

The method for monitoring the physiological condition of a patient is as follows: The patient's parameters, such as cardiac rhythm, respiration rate, pulse wave propagation rate, and the number of the patient's movements, are first measured and recorded. Additionally, the following parameters may be measured: ballistocardiogram, apnea, cardiac arrhythmia, the ratio of inhalation duration to exhalation duration during a given period of time, paradoxal respiration, cardiac and respiratory noises, an approaching asthma attack, snoring intensivity, etc.

The system of the invention can be preset by various parameters, such as:

increase in the number of arrhythmias, for patients suffering from heart arrhythmia, Surpassing the maximum number of arrhythmias preset by the doctor will generate an alarm.

increase in a child's body temperature. Since an increase of 1° C. causes an increase in cardiac rhythm of 10 beats per minute, a sudden increase in a child's heart rate will alert the one concerned.

increase in respiration rate. A change in the ratio of inhalation duration to exhalation duration and an increase of the noise made by a patient suffering from asthma, may indicate the possible approach of an attack.

Data relating to the normal limit conditions of a specific patient, for each parameter, is entered into the memory of the computer 13 or the microprocessor 23 serving the monitoring system. The system is then arranged at the patient's bed 20 (FIG. 2) for patients confined to a bed, or near an armchair 40 (FIG. 4) for patients who are able to sit.

In the first case, i.e., in the case of a patient confined to his bed, a ruler, plate or string detector and sensor unit is placed within the bed. The sensor or sensors are then connected to a processor. In order to record the patient's pulse wave shift and to enhance the monitoring sensitivity, several spaced-apart detectors and sensors are used.

The accuracy of measurement of the rate of pulse wave propagation depends on the distance between the sensors. Thus, in the process of taking such a measurement in an armchair, it is recommended to locate one of the sensors in the heart area, and another sensor near a hand or a foot. If signals are to be obtained from the patient's foot, it is necessary to connect the measuring devices either to a floor element near the armchair or to a foot support. If the signals are to be obtained from the patient's hand during work activity, said measuring devices may be arranged in a pen or in any other hand-held tool.

Upon actuation of the monitoring system, information regarding the patient's cardiac and respiration rhythms, the rate of pulse wave propagation and the number of patient body movements is processed and recorded.

A patient's body movements, heartbeats, respiratory movements, snoring and other mechanical movements and sounds are detected by the measuring devices, converted into electric signals, and transmitted to the microprocessor. In the microprocessor the signals are partly processed, encoded and transmitted to the computer to be finally processed. When necessary, the computer generates an alarm.

Depending on the location of the sensors, two main types of electric signals (FIG. 11) may be seen on the monitor screen. As shown in FIG. 11, curve a represents a signal from the patient's chest (ballistocardiographic signal), and curve b represents a signal from the patient's pelvic or femoral region.

The signal processing is advantageously performed in the following succession. In the first stage, those parts of the obtained signals are removed which are more than twice the average amplitude and which are associated with the patient's body movements. At this stage, the number and time of movements are separated. It is also possible to determine an additional parameter associated with the speed of movement, which parameter may also serve in the evaluation of a patient's condition.

Those signals which may be associated with cardiac and respiratory activity are then separated from the obtained signals by means of filtration in different spectral ranges.

The rate of pulse wave propagation for a cardiac signal can now be determined, as exemplified by the curves a and b shown in FIG. 11. On curves a and b, characteristic points at T1 and T2, t1 and t2 are separated, corresponding to the starting points of the cardiac cycle. The rate of pulse wave propagation for a heart signal is calculated from the equations:

$$V1 = \frac{T1 - t1}{A} \qquad V2 = \frac{T2 - t2}{A}$$

wherein:

V1 and V2 are the rates of pulse wave propagation determined for different cycles;

T1-t1 and T2-t2 are time shifts between the signals of corresponding sensors; and A is the distance between the sensors.

The rate of respiratory wave propagation can likewise be determined. However, since it is not a medical parameter and serves only for noise filtration, it is not shown in the drawings and equations.

Thereafter, the calculated wave propagation rates V1 and V2 are compared with the rates characteristic for the specific patient, which are preset or obtained from earlier measurement cycles. In cases where the calculated rates do not correspond to those characteristic of the patient, the corresponding cycles of cardiac and respiratory activity are withdrawn from consideration, thereby increasing the reliability of the obtained information (noise protection). Such erroneous signals are caused by a person's weak movements, which the system has not defined as obvious ones.

From the remaining signals, the cardiac cycle parameters are determined from the ballistocardiogram. The inhalation and exhalation times, as well as noises at different breathing stages, are separated from the respiration signal. These latter data are of interest, for instance, in asthma cases. The obtained parameters are compared with parameters characteristic for the specific patient, obtained earlier at the same time of day, stored with parameters physiologically permissible for the patient at this time of day, and displayed on the computer screen. In the event that one of the parameters or functions relating to these parameters surpasses the preset range, the computer or microprocessor will set off an alarm.

In the event that external vibrations are present, e.g., when the measurements are performed in a car or airplane, or when snoring noises are present, the evaluation of the signals will commence by removing therefrom those components which are well known to be associated with external vibrations or with snoring. In order to obtain information on such vibrations or snoring, at least one additional sensing means (not shown), is used. In cases where background vibrations and/or snoring noises are present, the signals from the additional sensor are substracted from the main signals.

The use of a ruler or string as a means for detecting mechanical vibrations permits improvement of the quality of the separated cardiac signal. It has been noticed that the use of a plate as large as the chest (approximately 60×70 cm) reduces the signal-to-noise ratio of the cardiac signal, since the plate collects the noise during breathing from the entire volume of the lungs. When one of the plate dimensions is reduced to the dimensions of the ruler, e.g., 2×70 cm, the signal-to-noise ratio increases and the cardiac signal separation improves.

This is shown in FIG. 12, wherein cardiac signals are shown as obtained after filtration in an 11–30 cycle frequency range with the same patient. The signals of curve a were obtained by using a ruler-type detector, and the signals of curve b were obtained by using a plate-type detector. Points M1 are the signal amplitudes and points M2 are noise amplitudes. As is clearly seen in the figures, the signals obtained by using a plate-type detector are noisier.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A system for monitoring of a patient's physiological condition, comprising:

means for measuring the mechanical activity of a patient's body, including at least one means for detecting mechanical vibrations and transmitting the same to one or more sensing elements for converting the mechanical vibrations into electric signals;

means for transmitting said electric signals;

means for processing said electric signals and separating therefrom cardiac, respiration and body movement signals;

means for determining the pulse wave propagation rate from said electric signals;

means for determining characteristics and parameters of cardiac and respiratory cycles, from said cardiac and respiration signals, respectively as well as for storing and displaying at least a portion of said characteristics and parameters;

means for comparing at least one of said determined parameters with a predetermined parameter; and means for actuating an alarm signal when said at least one of said determined parameters exceeds a preset range.

2. The system according to claim 1, wherein said means for detecting mechanical vibrations and said sensing element are made as an integral unit.

3. The system according to claim 2, wherein said means for measuring the mechanical activity of a body comprises at least two sensors.

4. The system according to claim 3, wherein said sensors are secured to, or made integral with, a common means for detecting mechanical vibrations.

5. The system according to claim 2, wherein said means for detecting mechanical vibration is incorporated into a pen or any other hand tool.

6. The system according to claim 1, wherein said means for detecting mechanical vibration comprises a plate or strip-like member.

7. The system according to claim 6, wherein said plate or strip-like member consists of at least two parts connected by a flexible element.

8. The system according to claim 6, wherein said plate or strip-like member comprises at least one structural feature of a bed or an armchair.

9. The system according to claim 6, wherein said plate or strip-like member is incorporated into a piece of bedding.

10. The system according to claim 6, wherein said plate or strip-like member comprises a floor element.

11. The system according to claim 1, wherein said means for transmitting mechanical vibrations comprises a string.

12. The system according to claim 1, wherein said sensing element comprises a crystal.

13. The system according to claim 12, wherein said crystal is a piezoelectric crystal.

14. The system according to claim 1, wherein said sensing element comprises piezoelectric ceramics.

15. The system according to claim 1, wherein said sensing element comprises a piezoelectric film.

16. The system according to claim 1, wherein said means for signal processing, means for determining the rate of pulse wave propagation, means for determining characteristics and parameters of cardiac and respiratory cycles, means for storing and displaying the characteristics and parameters, means for comparing at least one determined parameter with a predetermined parameter and means for actuating an alarm signal, comprise one of a computer and a microprocessor.

17. The system according to claim 1, wherein said means for transmitting electric signals comprises a wire, radio or infrared communication device.

18. A method of monitoring the physiological condition of a patient's body, comprising the steps of:

obtaining signals representing the mechanical activity and movement of the body from two or more detecting and sensing means not secured to the body and spaced apart from each other;

removing signals associated with the movements of the body from the obtained signals;

separating signals possibly associated with cardiac and/or respiratory activity from the obtained signals;

determining propagation rates of the pulse waves of cardiac and respiration activities by determining the shift of the obtained cardiac and respiration signals;

comparing the signals representing propagation rates with propagation rate signals obtained from an earlier measurement of the same body;

removing those signals which are not characteristic of the wave propagation rates of said body;

determining the cardiac and respiratory rhythm parameters from the remaining signals;

comparing said parameters with parameters obtained from an earlier measurement of the same body, as well as with predetermined parameters;

separating and removing parameters which differ from said predetermined parameters;

storing, displaying and comparing the separated parameters with parameters obtained from said earlier measurements, and generating an alarm when one of the parameters exceeds a preset range.

19. A method according to claim 1, further comprising the step of detecting and measuring signals associated with external vibrations and/or snoring.

20. A method according to claim 19, wherein the components known to be associated with external vibrations or snoring are measured by at least one additional measuring means.

* * * * *